(12) United States Patent
Niidome et al.

(10) Patent No.: US 7,595,168 B2
(45) Date of Patent: Sep. 29, 2009

(54) METHOD OF SCREENING FOR SUBSTANCES USEFUL FOR TRANSDIFFERENTIATION OF MICROGLIA INTO NEURONS

(75) Inventors: Tetsuhiro Niidome, Kyoto (JP); Satoru Matsuda, Osaka (JP); Takeshi Kihara, Kyoto (JP); Hachiro Sugimoto, Kyoto (JP)

(73) Assignee: Eisai R&D Management Co., Ltd., Bunkyo-ku (JP)

( * ) Notice: Subject to any disclaimer, the term of this patent is extended or adjusted under 35 U.S.C. 154(b) by 72 days.

(21) Appl. No.: 11/520,672

(22) Filed: Sep. 14, 2006

(65) Prior Publication Data

US 2008/0069806 A1    Mar. 20, 2008

(51) Int. Cl.
G01N 33/567 (2006.01)
G01N 33/53 (2006.01)
G01N 33/537 (2006.01)

(52) U.S. Cl. .................. 435/7.21; 435/7.1; 435/7.8; 435/7.92; 436/503

(58) Field of Classification Search .................. None
See application file for complete search history.

(56) References Cited

OTHER PUBLICATIONS

Matsuda et al. 2005, Soc. for Neuroscience meeting, abs. 831.2.*
Imai et al.; "Exogenous microglia enter the brain and migrate into ischaemic hippocampal lesions;" Neuroscience Letters; 272: 127-130 (1999).
Gehrmann et al.; "Microglia: instrinsic immuneffector cell of the brain;" Brain Research Reviews; 20: 269-287 (1995).
Yokoyama et al.; "Microglia, a Potential Source of Neurons, Astrocytes, and Oligodendrocytes;" GLIA; 45 (1): 96-104 (1988).
Wozney et al.; "Novel Regulators of Bone Formation: Molecular Clones and Activities;" Science; 242: 1528-1534 (1988).
Hogan; "Bone morphogenetic proteins: multifunctional regulators of vertebrate development;" Genes & Development; 10: 1580-1594 (1996).
Wine-Lee et al.; "Signaling through BMP type 1 receptors is required for development of interneuron cell types in the dorsal spinal cord;" Development; 131: 5393-5403 (2004).
Finley et al.; "BMP-4 Inhibits Neural Differentiation of Murine Embryonic Stem Cells;" J. Neurobiol.; 40: 271-287 (1999).
Nakashima et al.; "BMP2-mediated alteration in the developmental pathway of fetal mouse brain cells from neurogenesis to astrocytogenesis;" PNAS; 98: 5868-5873 (2001).
Ebendal et al.; "Bone Morphogenetic Proteins and Their Receptors: Potential Functions in the Brain;" J. Neurosci. Res.; 51: 139-146 (1998).
Miyazawa et al.; "Two major Smad pathways in TGF-β superfamily signalling;" Genes to Cells; 7: 1191-1204 (2002).
Miyazono et al.; "BMP receptor signaling: Transcriptional targets, regulation of signals, and signaling cross-talk;" Cytokine Growth Factor Rev.; 16: 251-263 (2005).
Yang et al.; "Bone morphogenetic protein-2 modulates Wnt and frizzled expression and enhances the canonical pathway of Wnt signaling in normal keratinocytes;" J. Dermatol. Sci.; 42: 111-119 (2006).
Miriyala et al.; "Bone Morphogenic Protein-4 Induces Hypertension in Mice: Role of Noggin, Vascular NADPH Oxidases, and Impaired Vasorelaxation;" Circulation; 113: 2818-2825 (2006).
Takeda et al.; "Molecular Cloning of Rat Bone Morphogenetic Protein BME Type IA Receptor and its Expression During Ectopic Bone Formation Induced by BMP;" Biochem. Biophys. Res. Commum.; 204: 203-209 (1994).
Strausberg et al.; "Generation and initial analysis of more than 15,000 full-length human and mouse cDNA sequences"; PNAS; 99: 16899-16903 (2002).
Mundy et al.; "Stimulation of Bone Formation in Vitro and in Rodents by Statins;" Science; 286: 1946-1949 (1999).
Ionescu et al.; "CREB Cooperates With BMP-Stimulated Smad Signaling to Enhance Transcription of the Smad6 Promoter," Journal of Cellular Physiology; 198: 428-440 (2004).
Logeart-Avramoglou et al.; "An assay for the determination of biologically active bone morphogenetic proteins using cells transfected with an inhibitor of differentiation promoter-luciferase construct;" Analytical Biochemistry; 349: 78-86 (2006).
Attisano et al.; "Activation of Signalling by the Activin Receptor Complex;" Molecular and Cellular Biology; 16: 1066-1073 (1996).
Pera et al.; "Integration of IGF, FGF, and anti-BMP signals via Smad1 phosphorylation in neural induction;" Genes & Development; 17: 3023-3028 (2003).
Wu et al.; "Heteromeric and Homomeric Interactions Correlate with Signaling Activity and Functional Cooperativity of Smad3 And Smad4/DPC4;" Molecular and Cellular Biology; 17: 2521-2528 (1997).
Gong et al.; "Regulation of phosphorylation of neuronal microtubule-associated proteins MAP1b and MAP2 by protein phosphatase-2A and -2B in rat brain;" Brain Research; 853: 299-309 (2000).
Cagnin et al.; "In vivo evidence for microglial activation in neurodegenerative dementia;" ACTA Neurologica Scandinavica; 114 (Suppl. 185): 107-114 (2006).
Fujimoto et al.; "Acarbose-induced hepatic injury;" The Lancet; 351: 340-341 (1998).
Winkler et al.; "Intranigral Transplants of GABA-Rich Striatal Tissue Induce Behavioral Recovery in the Rat Parkinson Model and Promote the Effects Obtained by Intrastriatal Dopaminergic Transplants;" Exp. Neurol.; 155: 165-186 (1999).
Glodzik-Sobanska et al.; "GABA in ischemic stroke. Proton magnetic resonance study;" Med Sci Monit; 10 (Suppl. 3): 88-93 (2004).
Green et al.; "GABA potentiation: a logical pharmacological approach for the treatment of acute ischaemic stroke;" Neuropharmacology; 39: 1483-1494 (2000).
Melone et al.; "Huntington's Disease: New Frontiers for Molecular and Cell Therapy;" Curr Drug Targets; 6: 43-56 (2005).

(Continued)

*Primary Examiner*—Olga N Chernyshev
(74) *Attorney, Agent, or Firm*—Oliff & Berridge, PLC

(57) ABSTRACT

According to the present invention, there is provided a method of screening for a substance useful for transdifferentiation of microglia into neurons, a method of producing neurons, and a method of treating a neurologic disorder.

14 Claims, 2 Drawing Sheets

OTHER PUBLICATIONS

Reynolds et al.; "Neurochemical-clinical correlates in Huntington's disease—applications of brain banking techniques;" J Neural Transm; 39: 207-214 (1993).

Weinstock; "The Pharmacotherapy of Alzheimer's Disease Based on the Cholinergic Hypothesis: an Update;" Neurodegeneration; 4: 349-356 (1995).

Juncos; "Levodopa: Pharmacology, Pharmacokinetics, and Pharmacodynamics;" Neurologic Clinics; 10: 487-509 (1992).

Saito et al; "Prolonged ectopic calcification induced by BMP-2-derived synthetic peptide;" J Biomed Mater Res A; 70: 115-121 (2004).

Kawabata et al.; "Signal Transduction by Bone Morphogenetic Proteins;" Cytokine & Growth Factor Reviews; 9: 49-61 (1998).

Sanchez-Ramos et al.; "Adult Bone Marrow Stromal Cells Differentiate into Neural Cells in Vitro;" Experimental Neurology; 164: 247-256 (2000).

Deng et al.; "In Vitro Differentiation of Human Marrow Stromal Cells into Early Progenitors of Neural Cells by Conditions That Increase Intracellular Cyclic AMP;" Biochem. Biophys. Res. Commun.; 282: 148-152 (2001).

Woodbury et al.; "Adult Rat and Human Bone Marrow Stromal Cells Differentiate Into Neurons;" J. Neuroscience Research; 61: 364-370 (2000).

Padovan et al.; "Expression of Neuronal Markers in Differentiated Marrow Stromal Cells and CD133 Stem-Like Cells;" Transplant; 12: 839-848 (2003).

Kim et al.; "Differentiation of adult bone marrow stem cells into neuroprogenitor cells in vitro;" NeuroReport; 13: 1185-1188 (2002).

Kohyama et al; "Brain from bone: Efficient "meta-differentiation" of marrow stromaderived mature osteoblasts to neurons with Noggin or a demethylating agent;" Differentiation; 68: 235-244 (2001).

ten Dijke et al.; "Controlling cell fate by bone morphogenetic protein receptors;" Molecular and Cellular Endocrinology; 211: 105-113 (2003).

Itsykson et al.; "Derivation of neural precursors from human embryonic stem cells in the presence of noggin;" Molecular and Cellular Neuroscience; 30: 24-36 (2005).

Pera et al.; "Regulation of human embryonic stem cell differentiation by BMP-2 and its antagonist noggin;" J. Cell Sci.; 117: 1269-1280 (2004).

Lim et al.; "Noggin Antagonized BMP Signaling to Create a Niche for Adult Neurogensis;" Neuron; 28: 713-726 (2000).

Kondo et al.; "A role for Noggin in the development of oligodendrocyte precursor cells;" Developmental Biology; 267: 242-251 (2004).

Rios et al.; "Bmp2 antagonizes sonic hedgehog-mediated proliferation of cerebellar granule neurons through Smad5 signalling;" Development; 131: 3159-3168 (2004).

Matsuda, S. et al. "Transdifferentiation of microglia into GABAergic neurons induced by serum in vitro," *Neuroscience 2005*, p. 831.2.

* cited by examiner

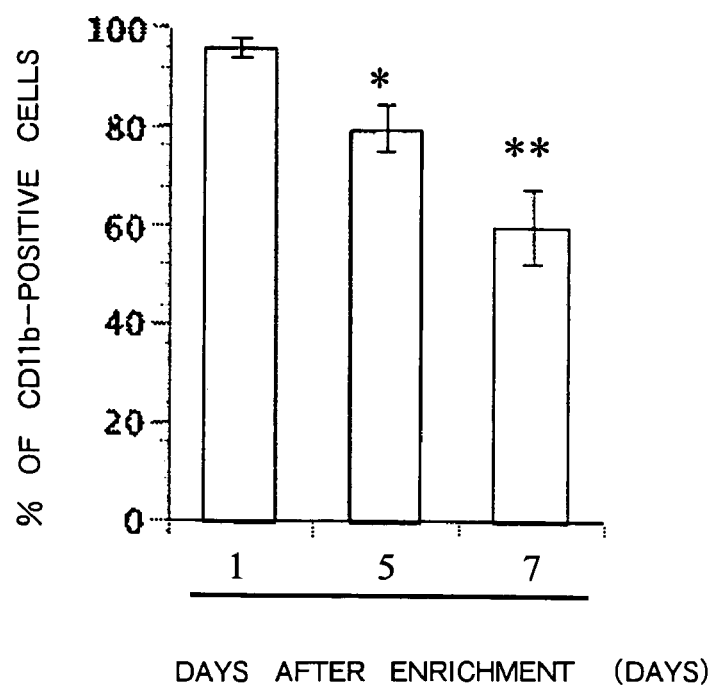
F I G. 1A
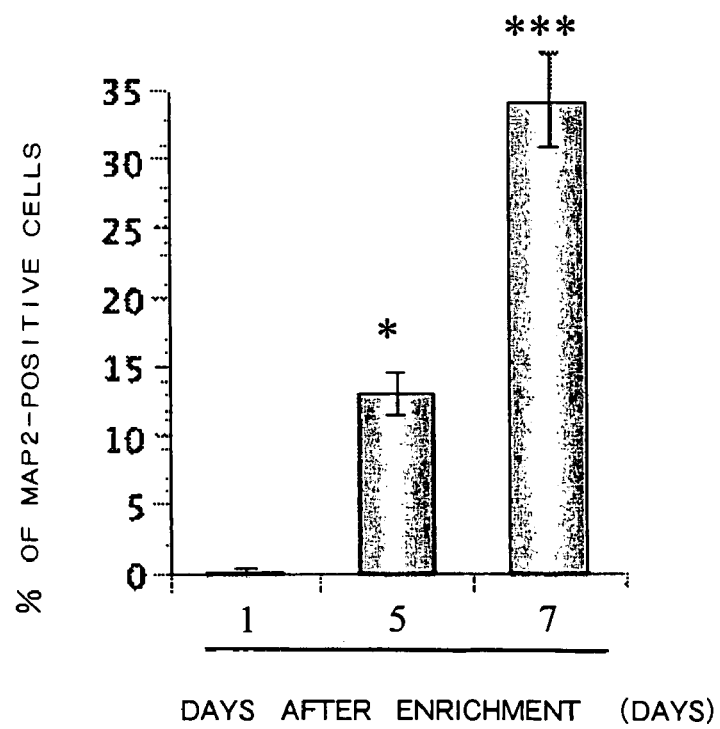
F I G. 1B

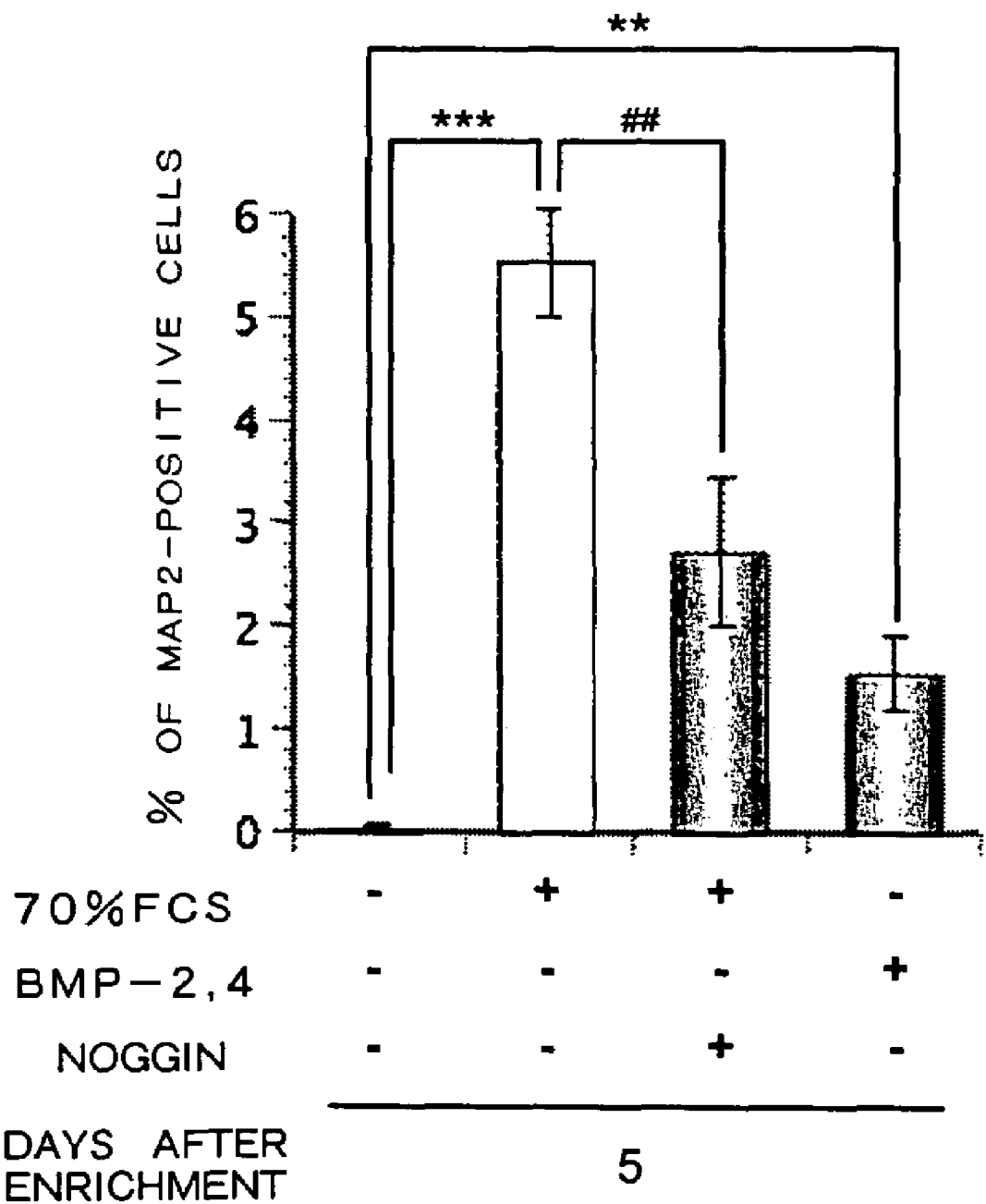
F I G. 2

METHOD OF SCREENING FOR SUBSTANCES USEFUL FOR TRANSDIFFERENTIATION OF MICROGLIA INTO NEURONS

BACKGROUND OF THE INVENTION

1. Field of the Invention

The present invention relates to a method of screening for a substance useful for transdifferentiation of microglia into neurons, a method of producing neurons, and a method of treating a neurologic disorder.

2. Background Technology

The regenerative therapy in cerebral and neurological fields refers to the differentiation of cells having the capability to differentiate into neurons and its application to therapy. The cells used have been mainly neural stem cells and ES cells. On the other hand, microglia, one of glia cells in the central nervous system, are considered to be more suitable for use in the regenerative therapy than neural stem cells or ES cells because of, for example, the following reasons: (1) a patient can use his/her own cells, which causes fewer ethical problems, (2) the number of neurons to be differentiated will be large since the number of microglia is extremely large, and (3) there is no need for concern about the migration of differentiated cells toward lesions since microglia themselves have a feature to migrate toward lesions (Imai, F. et al., Neuroscience Letters 272:127-130 (1999), Gehrmann, J. et al., Brain Research Reviews 20:269-287 (1995)). To date, the use of serum has been reported as a means to transdifferentiate microglia into neurons (Yokoyama A. et al., Glia 45(1):96-104 (2004)).

Meantime, bone morphogenetic protein (hereinafter referred to as "BMP") was originally identified as a protein which controls the formation of cartilage and bone (Wozney J M. et al., Science 242:1528-1534 (1988)). Further, BMP is known to act also on monocytes, epithelial cells, mesenchymal cells, and neural cells and plays a central role in the morphogenesis of various tissues and organs by controlling the growth, differentiation, migration, and apoptosis of these cells (Hogan B L M. et al., Genes Dev 10:1580-1594 (1996)). To date, it has been reported that the signals from the BMP receptor IA are essential for the development of intervening neurons of spinal cord (Wine-Lee L. et al., Development 131:5393-5403 (2004)), that BMP-4 suppresses the production of neurons in the fetal brain (Finleg M F. et al., J. Neurobiol. 40:271-287 (1999)) and that BMP-2 mediates switching from neuron production to astrocyte production (Nakashima K. et al., PNAS 98:5868-5873 (2001)).

SUMMARY OF THE INVENTION

An objective of the present invention is to provide a method of screening for a substance useful for transdifferentiation of microglia into neurons, a method of producing neurons, and a method of treating a neurologic disorder.

According to the present invention, there is provided a method of screening for a substance useful for transdifferentiation of microglia into neurons, comprising the step of detecting the BMP signal transduction enhancing activity of a test substance (hereinafter occasionally referred to as a "screening method according to the present invention").

According to the present invention, there is also provided a method of producing neurons, comprising the step of bringing a substance having a BMP signal transduction enhancing activity into contact with microglia to transdifferentiate microglia into neurons (hereinafter occasionally referred to as a "production method according to the present invention").

According to the present invention, there is further provided a method of treating a neurologic disorder, comprising the step of administering a pharmaceutical composition comprising a substance having a BMP signal transduction enhancing activity to a mammal, including a human (hereinafter occasionally referred to as a "therapeutic method according to the first embodiment of the present invention").

According to the present invention, there is furthermore provided a method of treating a neurologic disorder, comprising the step of transplanting neurons produced by the production method according to the present invention into a mammal, including a human (hereinafter occasionally referred to as a "therapeutic method according to the second embodiment of the present invention").

According to the present invention, a substance which can induce transdifferentiation into neurons from microglia but not from neural stem cells or ES cells can be screened and the substance obtained by this screening can be used in regenerative therapy. When microglia are used in regenerative therapy, a patient can use his/her own cells, which causes fewer ethical problems. Further the number of neurons to be differentiated will be large since the number of microglia is extremely large. Further, there is no need for concern about the migration of differentiated cells toward lesions when microglia are used for regenerative therapy. As mentioned above, a substance which transdifferentiates microglia into neurons is greatly useful in regenerative therapy as compared to a substance which transdifferentiates neural stem cells or ES cells into neurons and thus the present invention is expected to greatly contribute to promote the realization of regenerative therapy.

BRIEF DESCRIPTION OF THE DRAWINGS

FIG. 1 shows the increase in the number of MAP-positive cells by serum (Example 1). In the figure, *, , and * denote that there is a significant difference from data for untreated microglia (day 1) at levels of $p<0.05$, $p<0.01$, and $p<0.001$, respectively (Dunnett's test).

FIG. 2 shows the action of BMP on transdifferentiation of microglia into neurons (Example 2). In the figure,  and * denote that there is a significant difference from data for a negative control at levels of $p<0.01$ and $p<0.001$, respectively (Student's t-test). Further, ## denotes that there is a significant difference from data for a positive control at a level of $p<0.01$ (Student's t-test).

DETAILED DESCRIPTION OF THE INVENTION

The present invention will be explained in detail below. The following description is merely exemplary to explain the present invention and is not intended to limit the invention only to the described embodiments. All technical terms, scientific terms, and professional terms used in this specification mean the same as those generally understood by those ordinary skilled in the art in the technical field of the present invention and are used only for the purpose of explaining a specific embodiment but not intended to limit the scope of the invention. The present invention can be carried out in various modes of embodiments without departing from the spirit and scope of the invention.

All the literature, publications, patent publications, and other patent literature cited in this specification are incorporated in the specification by reference and can be used for carrying out the present invention.

Screening Method

The present inventors have confirmed that microglia can be transdifferentiated into neurons by treating the microglia with BMP (Example 2). The present inventors have also confirmed that transdifferentiation of microglia into neurons is suppressed by a BMP inhibitor (Example 2). From the results above, it has been revealed that the transdifferentiation of microglia into neurons is controlled by BMP signal transduction, namely, that microglia can be transdifferentiated into neurons by enhancing the BMP signal transduction. The present invention is based on these findings. Namely, according to the present invention, a substance useful for transdifferentiation of microglia into neurons can be screened by identified whether or not the BMP signal transduction is enhanced using individual signals in the BMP signal transduction pathway as indices.

The screening method according to the present invention is advantageous in such a respect that a drug for the treatment of a neurologic disorder can be developed utilizing a mechanism different from that of conventional drugs, in which microglia are transdifferentiated into neurons. Further, it is advantageous in such a respect that a substance useful for transdifferentiation of microglia into neurons can be screened utilizing a mechanism of the BMP signal transduction which is well known to those skilled in the art.

In the present specification, the term "BMP signal transduction" refers to signal transduction generated by binding of BMP to a BMP receptor. Since the BMP is a protein which belongs to the TGF-β superfamily, the BMP receptor forms a heteromeric complex consisting of a type-I receptor and a type-II receptor in the same manner as a TGF-β receptor. When BMP, a ligand, is bound, the type-II receptor first phosphorylates the type-I receptor for activation. The activated type-I receptor phosphorylates R-Smads. Here, the R-Smads are different in each subclass of the TGF-β superfamily and Smad1, Smad5, and Smad8 function as an R-Smad in the BMP signal transduction pathway. The phospholylated R-Smads form heteromeric complexes (Smad complexes) with Smad4, called Co-Smad, and translocate to the nucleus. In the nucleus, the Smad complexes bind directly or along with other transcription factors to the promoter region of a BMP target gene and regulate its transcription activity (Ebendal T. et al., J. Neurosci. Res. 51:139-146 (1998), Miyazawa K. et al., Genes Cells 7:1191-1204 (2002), Miyazono K. et al., Cytokine Growth Factor Rev. 16:251-263 (2005)). Examples of the BMP target gene include Id1-3, Smad6, Smad7, OASIS, Prx2, TIEG, Snail, Vent-2, and Tlx-2. Here, Smad6 and Smad7 are called I-Smads and control BMP signaling in a negative feedback mode.

In the present specification, a method for "detecting the BMP signal transduction enhancing activity of a test substance" is not particularly limited as long as it can detect or measure the extent of the BMP signal transduction. For example, a method for detecting or measuring the extent of BMP expression or a method for detecting or measuring the extent of BMP receptor activation can be used.

The amino acid sequence and the gene sequence for BMPs and the amino acid sequence and the gene sequence for BMP receptors have been reported for various species (Yang L. et al., J. Dermatol. Sci. 42:111-119 (2006), Miriyala S. Circulation 113:2818-2825 (2006), Takeda K. et al., Biochem. Biophys. Res. Commun. 204:203-209 (1994), Strausberg R L. et al., PNAS 99:16899-16903 (2002)) and these publications can be appropriately referred to upon carrying out embodiments of the present invention. Gene Bank accession numbers for the disclosed sequence information are exemplified as follows:

Human BMP-2: NM_001200
Human BMP-4: NM-001202, NM_130850, NM_130851
Rat BMP receptor IA: NM_030849
Human BMP receptor II: BC043650
Rat BMP receptor II: AB073714

According to a first embodiment of the screening method of the present invention, the BMP signal transduction enhancing activity of a test substance can be detected by detecting the BMP expression.

In the first embodiment, the BMP expression can be detected by the step of (a) detecting the BMP expression in a test cell in the presence and in the absence of the test substance. After the step (a), the step of (b) comparing the amount of the BMP expression in the presence and in the absence of the test substance can further be included. When the BMP expression is increased by the addition of the test substance, the amount of BMP binding to the BMP receptor is also increased and the BMP signal transduction is enhanced so that said test substance can be identified as a substance having BMP signal transduction enhancing activity, namely, as a substance useful for transdifferentiation of microglia into neurons.

For the detection of the BMP expression, for example, the reporter assay method (Mundy, G. et al., Science 286:1946-1949 (1999)) and the Western blotting method can be used.

In the case where the reporter assay method is used, the BMP expression can be detected by the step of (a-1) detecting expression of a reporter gene in a cell containing a BMP receptor which has been transfected with a recombinant vector comprising a promoter gene for the BMP gene and the reporter gene in the presence and in the absence of the test substance.

After the step (a-1), the step of (b-1) comparing the amount of the reporter gene expression in the presence and in the absence of the test substance can further be included.

In the step (b-1), since the reporter gene expression can be an index for the BMP expression, when the amount of the reporter gene expression detected in the presence of the test substance exceeds, preferably more than about 3 times, more preferably more than about 10 times, the amount of the reporter gene expression detected in the absence of the test substance, said test substance can be identified as a substance which increases the BMP expression, namely, as a substance useful for transdifferentiation of microglia into neurons.

According to a second embodiment of the screening method of the present invention, the BMP signal transduction enhancing activity of a test substance can be detected by detecting BMP receptor activation.

In the second embodiment, the BMP receptor activation can be detected by the step of (c) detecting the BMP receptor activation in a cell containing a BMP receptor in the presence and in the absence of the test substance. After the step (c), the step of (d) comparing the amount of BMP receptor activation in the presence and in the absence of the test substance can further be included. When the BMP receptor is activated by the addition of the test substance, the BMP signal transduction is enhanced so that said test substance can be identified as a substance having BMP signal transduction enhancing activity, namely, as a substance useful for transdifferentiation of microglia into neurons.

Detection of the activation of the BMP receptor can be carried out by detecting various signals in the BMP signal transduction pathway. Examples of the various signals in the BMP signal transduction pathway include phosphorylation of type-I receptors, phosphorylation of R-Smads, formation of complexes of R-Smads with Co-Smad, and transcription activity of a BMP target gene, and the BMP receptor activation can be detected using these signals as an index.

In the case where the activation of the BMP receptor is detected using transcription activity of the BMP target gene as an index, the BMP receptor activation can be detected by the step of (e) detecting the transcription activity of a BMP target gene in a cell containing a BMP receptor in the presence and in the absence of the test substance. After the step (e), the step of (f) comparing the amount of the transcription activity of the BMP target gene in the presence and in the absence of the test substance can further be included.

In the case where the transcription activity of the BMP target gene is used as an index, the reporter assay method (Ionescu, A. M. et al., Journal of Cellular Physiology 198: 428-440 (2004)), the Western blotting method, and the like can be used.

In the case where the reporter assay is used, for example, the transcription activity of the BMP target gene can be detected by the step of (e-1) detecting the expression of a reporter gene in a cell containing a BMP receptor which has been transfected with a recombinant vector comprising a gene comprising a BMP-responsive sequence in a promoter for the BMP target gene and the reporter gene in the presence and in the absence of the test substance.

After the step (e-1), the step of (f-1) comparing the amount of the reporter gene expression in the abovementioned cell in the presence and in the absence of the test substance can further be included.

In the step (f-1), the expression of the reporter gene is used as an index for the transcription activity of the BMP target gene. Since the transcription activity of the BMP target gene is one of signals generated by BMP receptor activation and indicates the BMP receptor activation, when the amount of the reporter gene expression detected in the presence of the test substance exceeds, preferably more than about 3 times, more preferably more than about 10 times, the amount of the reporter gene expression detected in the absence of the test substance, said test substance can be identified as a substance which activates the BMP receptor, namely, as a substance useful for transdifferentiation of microglia into neurons.

The BMP target gene can be selected from the gene group consisting of Id1-3, Smad6, Smad7, OASIS, Prx2, TIEG, Snail, Vent-2, and T1x-2, preferably the Smad6 gene.

In the present specification, the "gene comprising a BMP-responsive sequence" means a gene comprising a BMP-responsive sequence present in a promoter for a target gene. Anyone skilled in the art can specify the BMP-responsive sequence present in a promoter based on known BMP gene sequences (Logeart-Avramoglou D. Anal. Biochem. 349:78-86 (2005)). Smad complexes can regulate the transcription activity by binding to this site.

In the present specification, examples of the "reporter gene" include the alkaline phosphatase gene and the luciferase gene.

In the present specification, the "cell containing a BMP receptor" is not particularly limited and can be any cell as long as it contains a BMP receptor and can detect the BMP receptor activation, namely, various signals in the BMP signal transduction, preferably, microglia.

In the case where the BMP receptor activation is detected using phosphorylation of a type-I BMP receptor as an index, the BMP receptor activation can be detected by the step of (g) detecting the phosphorylation of the type-I BMP receptor in a cell containing a BMP receptor in the presence and in the absence of the test substance. After the step (g), the step of (h) comparing the amount of the phosphorylation of the type-I BMP receptor in the presence and in the absence of the test substance can further be included.

In the case where the phosphorylation of the type-I BMP receptor is used as an index, the autoradiography method (Attisano L. et al., Mol. Cell. Biol. 16:1066-1073 (1996)) and the like can be used.

The phosphorylation of the type-I BMP receptor is one of the signals generated by the BMP receptor activation and indicates the BMP receptor activation. Accordingly, in the step (h), when the amount of the phosphorylation detected in the presence of the test substance exceeds, preferably more than about 3 times, more preferably more than about 10 times, the amount of the phosphorylation detected in the absence of the test substance, said test substance can be identified as a substance which activates the BMP receptor, namely, as a substance useful for transdifferentiation of microglia into neurons.

In the case where the BMP receptor activation is detected using phosphorylation of R-Smad as an index, the BMP receptor activation can be detected by the step of (i) detecting the phosphorylation of R-Smad in a cell containing a BMP receptor in the presence and in the absence of the test substance. After the step (i), the step of (j) comparing the amount of the phosphorylation of R-Smad in the presence and in the absence of the test substance can further be included.

In the case where the phosphorylation of R-Smad is used as an index, the autoradiography method (Pera E M. et al., Gene Dev. 17:3023-3028 (2003)) and the like can be used.

The phosphorylation of R-Smad is one of the signals generated by the BMP receptor activation and indicates the BMP receptor activation. Accordingly, in the step (j), when the amount of the phosphorylation detected in the presence of the test substance exceeds, preferably more than about 3 times, more preferably more than about 10 times, the amount of the phosphorylation detected in the absence of the test substance, said test substance can be identified as a substance which activates the BMP receptor, namely, as a substance useful for transdifferentiation of microglia into neurons.

In the case where the BMP receptor activation is detected using the presence of a complex of R-Smad and Smad4 as an index, the BMP receptor activation can be detected by the step of (k) detecting the complex of R-Smad and Smad4 in a cell containing a BMP receptor in the presence and in the absence of the test substance. After the step (k), the step of (l) comparing the amount of the complex of R-Smad and Smad4 in the presence and in the absence of the test substance can further be included.

In the case where the presence of the complex of R-Smad and R-Smad is used as an index, the immunoprecipitation method, the two-hybrid method (Wu R Y. et al., Mol. Cell. Biol. 17:2521-2528 (1997)), and the like can be used.

The formation of the complex of R-Smad and Smad4 is one of the signals generated by the BMP receptor activation and makes an index for the BMP receptor activation. Accordingly, in the step (l), when the amount of the complexes in the presence of the test substance exceeds, preferably more than about 3 times, more preferably more than about 10 times, the amount of the complex in the absence of the test substance, said test substance can be identified as a substance which activates the BMP receptor, namely, as a substance useful for transdifferentiation of microglia into neurons.

According to the present invention, the accuracy of screening can be increased by further carrying out the step of bringing the test substance having BMP signal transduction enhancing activity thus obtained into contact with microglia and then detecting MAP2 protein expression in said microglia.

The MAP2 protein expression can be detected by the step of (m) bringing the test substance having BMP signal transduction enhancing activity obtained by the screening method according to the present invention into contact with microglia in the presence and in the absence of the test substance and then detecting the MAP2 protein expression in said microglia. A method for the detection is not particularly limited as long as it can quantitatively measure the MAP2 protein expression. For example, the Western blotting method (Gong C X. et al., Brain Res. 24; 299-309(2000)) can be used.

After the step (m), the step of (n) comparing the amount of the MAP2 protein expression in the presence and in the absence of the test substance can further be included.

The MAP2 protein is an index indicative of neurons (Example 1). Accordingly, in the step (n), when the amount of the MAP2 protein expression in the presence of the test substance exceeds, preferably more than about 3 times, more preferably more than about 10 times, the amount of the MAP2 protein expression in the absence of the test substance, said test substance can be identified with a high accuracy as a substance useful for transdifferentiation of microglia into neurons.

In the present specification, examples of the "test substance" include, but are not limited to, low molecular weight synthetic compounds, proteins, synthetic peptides, purified or partially purified polypeptides, antibodies, bacterial releasing substances (including bacterial metabolic products), and nucleic acids (e.g., antisense strands, ribozymes, RNAis), preferably low molecular weight synthetic compounds. The "test substance" can be either a novel substance or a known substance.

Production Methods

According to Example 2, it has been found that transdifferentiation of microglia into neurons is controlled by BMP signal transduction, namely microglia can be transdifferentiated into neurons by enhancing the BMP signal transduction. Accordingly, neurons can be produced by bringing a substance having BMP signal transduction enhancing activity into contact with microglia to induce the transdifferentiation of microglia into neurons.

Here, examples of the "substance having BMP signal transduction enhancing activity" include a substance which is identified to be useful for transdifferentiation of microglia into neurons according to the screening method of the present invention and BMP.

Further, "bringing into contact" can be carried out by adding a substance having BMP signal transduction enhancing activity to culture cells containing microglia, or by administering a substance having BMP signal transduction enhancing activity (especially a substance with a high blood-brain barrier permeability) to a mammal, including a human.

Examples of the production method according to the present invention include a method for carrying out the transdifferentiation of microglia into neurons in vitro by adding a substance having BMP signal transduction enhancing activity as well as a method for carrying out the transdifferentiation of microglia into neurons in vivo (especially in the brain) by administering a substance having BMP signal transduction enhancing activity to a mammal, including a human.

In the production method according to the present invention, in which the transdifferentiation is carried out in vitro, the step of culturing transdifferentiated neurons for multiplication can further be included.

Therapeutic Methods

According to Example 2, transdifferentiation of microglia into neurons can be carried out by enhancing BMP signal transduction. Since neurons transdifferentiated from microglia can produce various neural substances, they can be used for the treatment of a neurologic disorder. Accordingly, a neurologic disorder can be prevented and/or treated by using a substance having the BMP signal transduction enhancing activity or by using neurons produced using said substance.

According to a first embodiment of the therapeutic method of the present invention, a neurologic disorder can be prevented and/or treated by administering a pharmaceutical composition comprising a substance having BMP signal transduction enhancing activity to a mammal, including a human to transdifferentiate microglia in the brain into neurons which produce various neural substances whose productions have been lowered.

Specifically, the pharmaceutical composition comprising a substance having BMP signal transduction enhancing activity can be administered to a patient after confirming accumulation of microglia at a lesion in the brain.

Here, examples of the "substance having BMP signal transduction enhancing activity" include a substance which is identified as a substance useful for transdifferentiation of microglia into neurons by the screening method according to the present invention and BMP.

Further, the "substance having BMP signal transduction enhancing activity" is preferably a substance having a high permeability into the brain when administered directly to a patient.

The mode of administration can be oral, parenteral (e.g., intravenous, by inhalation, topical application), preferably oral administration.

The accumulation of microglia at a lesion can be confirmed by positron emission tomography (PET) using a radioactive ligand which binds to active type microglia ([11C](R)-PK11195) (Cagnin, A. et al., Acta Neurol Scand Suppl. 185: 107-114 (2006)). Therapeutic effect can be enhanced by carrying out the administration at the time when microglia accumulate at a lesion so that transdifferentiation can be carried out with enough number of microglia to be transdifferentiated into neurons.

Forms of pharmaceutical compositions for oral and parenteral administration and methods for their production are known by those skilled in the art. For example, a substance having BMP signal transduction enhancing activity can be mixed with pharmaceutically acceptable carriers and the like according to a general method.

The dose of a substance having BMP signal transduction enhancing activity can be determined by a clinician based on various factors such as the route of administration, the kind of disease, the severity of the symptom, the age, sex, and bodyweight of the patient, the kind of salt, the specific type of disease, pharmacological features such as the drug kinetics and toxicological characteristics, involvement of drug delivery system, and whether administered as a part of a combination with other medicines.

According to a second embodiment of the therapeutic method of the present invention, a neurologic disorder can be prevented and/or treated by the production of various neural substances whose production have been lowered, by transplanted neurons.

The therapeutic method according to the present invention can be carried out by obtaining cells potentially containing microglia from a mammal, preferably from an individual who himself/herself receive transplantation, bringing the cells thus obtained into contact with a substance having BMP signal transduction enhancing activity to transdifferentiate microglia into neurons, and transplanting the neurons into the mammal from which the microglia are obtained.

Here, the neurons thus obtained can be transplanted into the brain, preferably at a lesion site.

In the therapeutic method according to the present invention, neurons utilized are transdifferentiated from microglia which are advantageously present in a large amount. Further, microglia themselves advantageously have a feature to migrate to lesions.

According to Example 2, by enhancing the BMP signal transduction, microglia can be transdifferentiated into neurons, such as GABA nervous system neurons, acetylcholine nervous system neurons, and dopamine nervous system neurons.

Accordingly, examples of the neurologic disorder to be treated by the therapeutic method of the present invention include neurologic disorders caused by dysfunction of the GABA nervous system, neurologic disorders caused by dysfunction of the acetylcholine nervous system, and neurologic disorders caused by dysfunction of the dopamine nervous system.

Examples of the neurologic disorders caused by dysfunction of the GABA nervous system, namely the neurologic disorders caused by dysfunction of GABAergic neurons include Parkinson's disease (Penn, R. D. et al., Lancet 351: 340-341 (1998), Winkler, C. et al., Exp Neurol. 155:165-186 (1999)), cerebral infarction (Glodzik-Sobanska, L. et al., Med Sci Monit. 10:88-93 (2004), Green, A. R. et al., Neuropharmacology 39:1483-1494 (2000)), and Huntington disease (Melone, M. A. et al., Curr Drug Targets 6:43-56 (2005), Reynolds, G. P. et al., J Neural Transm Suppl. 39:207-214 (1993)).

Examples of the neurologic disorders caused by dysfunction of the acetylcholine nervous system, namely the neurologic disorders caused by dysfunction of acetylcholinergic neurons include Alzheimer's disease (Weinstock, M., Neurodegeneration 4:349-356 (1995)).

Examples of the neurologic disorders caused by dysfunction of the dopamine nervous system, namely the neurologic disorders caused by dysfunction of dopaminergic neurons include Parkinson's disease (Juncos, J. L., Neurol Clin 10:487-509 (1992)).

EXAMPLES

Example 1

Increase in the Number of MAP-Positive Cells by Serum

1. Culture of Microglia Obtained from Rats

The cerebral cortex was isolated from newborn Wistar rats aged from 0 to 1 day (obtained from Shimizu Experimental Material Co. Ltd.) and cultured in an Eagle's minimum essential medium (EMEM) supplemented with 10% fetal calf serum (FCS) and 5 mg/ml insulin at 37° C. in an atmosphere of 5% $CO_2$. After 14 to 16 days of incubation, microglia were isolated and prepared by the enriching procedure.

2. Transdifferentiation of Microglia into Neurons

The purified microglia were inoculated at a cell density of $8.7 \times 10^4$ cells/cm² and grown in a Dulbecco's modified essential medium (DMEM) supplemented with 10% FCS and 10 ng/ml M-CSF for 1 day (day 1) or for 3 days. Next, the cells were sustained in a de-differentiation-inducing medium (DMEM supplemented with 70% FCS and 10 ng/ml M-CSF) for 2 days, after which (on day 5) the cells were sustained in a differentiation-inducing medium (DMEM containing 10 mM HEPES, 4.5 mg/ml glucose, 5 μg/ml insulin, 5 nM sodium selenite, 5 μg/ml transferrin, 0.2 mg/ml bovine serum albumin, and 10 ng/ml IGF-1) for 2 days (day 7).

3. Immunocytochemical Study

The cells were fixed with 4% paraformaldehyde and then reacted individually with an anti-CD11b antibody (rabbit anti-MAP2 polyclonal antibody (AB5622), Chemicon International) or an anti-MAP2 antibody (rabbit anti-GFAP polyclonal antibody (Z0334), DakoCytomation) as a primary antibody and with Cy2-conjugated goat anti-mouse IgG (H+L) (Jackson ImmunoResearch) or Cy3-conjugated goat anti-rabbit IgG (H+L) (Jackson ImmunoResearch) as a secondary antibody. The CD11b is a marker for microglia and the MAP2 is a marker for neurons. Nucleus staining was carried out with 4',6'-diamidino-2-phenylindole (DAPI) and observation was made using a fluorescent microscope.

4. Quantification of cells positive for various markers

After immunostaining the cells, images (200× magnification) of 8 fields per case were randomly obtained using a fluorescent microscope and MataMorph software (Molecular Devices). The numbers of cells expressing individual markers were counted and the average rates to the total number of cells were used as data.

5. Results

By the treatment with 70% serum and the differentiation-inducing medium, the rates of the number of CD11b-positive cells to the total number of the cells (DAPI-positive cells) were 95.9±2.1% on day 1, 79.6±4.8% on day 5, and 59.8±7.6% on day 7 after enrichment, which showed a significant decrease with time (FIG. 1A). On the other hand, the rates of the number of MAP2-positive cells to the total number of cells were 0.2±0.2% on day 1, 13.0±1.5% on day 5, and 34.2±3.4% on day 7 after enrichment, which showed a significant increase with time (FIG. 1B).

From the results above, it was confirmed that microglia were transdifferentiated into neurons by the presence of the serum using the CD11b, a marker for microglia, and the MAP2, a marker for neurons, as indices.

Example 2

Action of BMP on Transdifferentiation of Microglia into Neurons

1. Culture of Microglia Obtained from Rats

Cells were cultured in the same manner as in Example 1.

2. Transdifferentiation of Microglia into Neurons

The purified microglia were inoculated at a cell density of $8.7 \times 10^4$ cells/cm² and grown in DMEM supplemented with 10% FCS and 10 ng/ml M-CSF for 3 days, after which the grown cells were sustained for 2 days (day 5) in the following 4 kinds of media: (1) a medium containing 10% FCS (negative control), (2) a medium containing 70% FCS (positive control), (3) a medium containing 70% FCS supplemented with 100 ng/ml noggin (a BMP inhibitor (N6784), Sigma), and (4) a medium containing 10% FCS supplemented with 10 ng/ml BMP-2 (B3555, Sigma) and 10 ng/ml BMP-4 (314-BP, R&D Systems).

3. Immunocytochemical Study

Study was carried out in the same manner as in Example 1.

4. Quantification of Cells Positive for Various Markers

Quantification was carried out in the same manner as in Example 1.

5. Results

On day 5 after enrichment, microglia were transdifferentiated into neurons by 70% serum (positive control) but this transdifferentiation was suppressed by noggin, a BMP inhibitor (FIG. 2). On the other hand, no microglia were transdifferentiated into neurons in the presence of 10% serum (negative control); however, microglia were transdifferentiated into neurons by the treatment with BMP (FIG. 2).

From the results above, it was revealed that BMP signaling controlled the transdifferentiation of microglia into neurons.

What is claimed is:

1. A method of screening for a substance useful for transdifferentiation of microglia into neurons, comprising:
   contacting a microglia cell with a test substance;
   measuring Bone Morphogenetic Protein (BMP) expression level or BMP receptor activation level in the microglia cell;
   comparing the BMP expression level or BMP receptor activation level in the presence of the test substance to BMP expression level or BMP receptor activation level in the absence of the test substance; and
   identifying the test substance as a substance useful for transdifferentiation of microglia into neurons when the test substance has an increased level of BMP expression or BMP receptor activation.

2. The method according to claim 1, wherein the BMP expression level is determined by measuring the expression level of a reporter gene wherein the microglia cell contains a BMP receptor and has been transfected with a recombinant vector comprising a promoter gene for the BMP gene and the reporter gene.

3. The method according to claim 1, wherein the BMP receptor activation level is determined by measuring the transcription activity level of a BMP target gene wherein the microglia cell contains a BMP receptor.

4. The method according to claim 1, wherein the BMP receptor activation level is determined by measuring the expression level of a reporter gene wherein the microglia cell contains a BMP receptor and has been transfected with a recombinant vector comprising a gene comprising a BMP-responsive sequence in a promoter for the BMP target gene and the reporter gene.

5. The method according to claim 3, wherein the BMP target gene is selected from the group consisting of Id1-3, Smad6, Smad7, OASIS, Prx2, TIEG, Snail, Vent-2, and T1x-2.

6. The method according to claim 4, wherein the BMP target gene is selected from the group consisting of Id1-3, Smad6, Smad7, OASIS, Prx2, TIEG, Snail, Vent-2, and T1x-2.

7. The method according claim 5, wherein the BMP target gene is the Smad6 gene.

8. The method according claim 6, wherein the BMP target gene is the Smad6 gene.

9. The method according to claim 2, wherein the reporter gene is an alkaline phosphatase gene or a luciferase gene.

10. The method according to claim 4, wherein the reporter gene is an alkaline phosphatase gene or a luciferase gene.

11. The method according to claim 1, wherein the BMP receptor activation level is determined by measuring the phosphorylation of a type-I BMP receptor wherein the microglia cell contains a BMP receptor.

12. The method according to claim 1, wherein the BMP receptor activation level is determined by measuring the phosphorylation of R-Smad wherein the microglia cell contains a BMP receptor.

13. The method according to claim 1, wherein the BMP receptor activation level is determined by measuring the complex of R-Smad and Smad4 wherein the microglia cell contains a BMP receptor.

14. The method according to claim 1, further comprising:
   contacting the identified test substance with a microglia cell;
   measuring the MAP2 protein expression level in the microglia cell;
   comparing the MAP2 protein expression level in the presence of the identified test substance to MAP2 expression level in the absence of the identified test substance; and
   confirming the identified test substance as a substance useful for transdifferentiation of microglia into neurons when the identified test substance has an increased level of MAP2 protein expression.

* * * * *